(12) United States Patent
Tsao et al.

(10) Patent No.: US 8,478,396 B2
(45) Date of Patent: Jul. 2, 2013

(54) PHOTOTHERAPY PATCH

(75) Inventors: Yu-Chia Tsao, Taipei (TW); Yi-Wen Yang, Taipei (TW); Jung-Chien Chang, Sanxia Township, Taipei County (TW)

(73) Assignee: Forward Electronics Co., Ltd. (TW)

( * ) Notice: Subject to any disclaimer, the term of this patent is extended or adjusted under 35 U.S.C. 154(b) by 0 days.

(21) Appl. No.: 13/552,921

(22) Filed: Jul. 19, 2012

(65) Prior Publication Data

US 2012/0283623 A1 Nov. 8, 2012

Related U.S. Application Data

(62) Division of application No. 12/805,739, filed on Aug. 18, 2010, now abandoned.

(30) Foreign Application Priority Data

Jun. 9, 2010 (TW) .............................. 99118800 A

(51) Int. Cl.
*A61N 1/30* (2006.01)
(52) U.S. Cl.
USPC ............................... 604/20; 604/180; 607/88

(58) Field of Classification Search
USPC ................... 604/20, 23, 180; 606/9; 607/1–3, 607/88, 91, 95
See application file for complete search history.

(56) References Cited

U.S. PATENT DOCUMENTS

| 7,480,530 | B2 * | 1/2009 | Sun et al. ........................ 604/20 |
| 7,507,228 | B2 * | 3/2009 | Sun et al. ...................... 604/501 |
| 2007/0043406 | A1 | 2/2007 | Tolkoff et al. |
| 2009/0204057 | A1 | 8/2009 | Woo et al. |
| 2010/0065834 | A1 | 3/2010 | Hammond |

FOREIGN PATENT DOCUMENTS

WO 2007141720 A1 12/2007

* cited by examiner

Primary Examiner — Theodore Stigell
(74) Attorney, Agent, or Firm — Bacon & Thomas, PLLC

(57) ABSTRACT

A phototherapy patch is disclosed, which includes: an adhesive layer, having a first surface and an opposite second surface; a pharmaceutical drug layer, disposed on the first surface of the adhesive layer; and a spontaneous emission layer, disposed over the pharmaceutical drug layer and capable of emitting therapeutic light by light illumination or a chemical reaction. Accordingly, the phototherapy patch according to the present invention has no power supply disposed therein, and thereby is suitable to be manufactured as a particularly thin and thus inconspicuous device.

11 Claims, 1 Drawing Sheet

PHOTOTHERAPY PATCH

This application is a divisional application of U.S. patent application Ser. No. 12/805,736, filed Aug. 18, 2010, now abandoned, (of which the entire disclosure of the prior application is hereby incorporated by reference).

BACKGROUND OF THE INVENTION

1. Field of the Invention

The present invention relates to a phototherapy patch and, more particularly, to a flexible phototherapy patch with no power supply disposed therein.

2. Description of Related Art

With the improvement of the quality of the life, the cosmetology industry has been developed quickly and home medical cosmetology has drawn more attention. Particularly, simpler and personally-operable cosmetological methods have been popular. In addition to conventional drugs and care products, phototherapy has been developed in medical cosmetology industry to more efficiently achieve a cosmetology or treatment object. A medicine journal reported that propionibacterium acnes, which cause redness and inflammation associated with acne, contain porphyrin, and free radicals can be generated by reaction between blue light (its wavelength ranges from about 400 nm to 470 nm) and porphyrin to eradicate propionibacterium acnes so as to reduce redness and inflammation associated with acne. In addition, red light (its wavelength ranges from about 600 nm to 700 nm) is helpful for wound healing and anti-inflammation; yellow light (its wavelength ranges from about 550 nm to 600 nm) can improve the circulation of skin cells and promote the regeneration of skin cells; and green light (its wavelength ranges from about 500 nm to 550 nm) can be used to regulate the function of skin glands and oil secretion and inhibit acne.

Many cosmetology related products have been commercially available for personal use. Among those, pharmaceutical patches are often used to treat facial wounds or acne. Besides conventional pharmaceutical patches, patch-type phototherapy systems, which is portable and can be self-applied by users, have been suggested. However, these suggested phototherapy patches have to be connected to a power supply to emit therapeutic light and thereby cannot be designed in a thin form.

Therefore, it is an important object of the present invention to develop a thin phototherapy patch.

SUMMARY OF THE INVENTION

The object of the present invention is to provide a phototherapy patch with no power supply disposed therein, which is advantageous to achieving slim design thereof and thereby is portable and can be self-applied by users.

To achieve the object, the present invention provides a phototherapy patch, including: an adhesive layer, having a first surface and an opposite second surface; a pharmaceutical drug layer, disposed on the first surface of the adhesive layer; and a spontaneous emission layer, disposed over the pharmaceutical drug layer and capable of emitting therapeutic light via light illumination or a chemical reaction.

Accordingly, the present invention can incorporate a spontaneous emission layer into the patch and maintain its thin appearance through thin film technology, such that combination of pharmaceutical drugs and phototherapy can achieve multiple therapeutic effects and accelerate therapy. Particularly, the phototherapy patch according to the present invention can emit therapeutic light via light illumination or a chemical reaction, and thus it is unnecessary to dispose a power supply in the phototherapy patch according to the present invention. Accordingly, the phototherapy patch according to the present invention is advantageous to achieving slim design and thereby is portable and can be self-applied by users.

In the present invention, the spontaneous emission layer may be a fluorescent layer, which can be driven via a chemical reaction and thereby emits therapeutic light. Alternatively, the spontaneous emission layer according to the present invention may include a solar absorption layer and an organic emission layer to be driven via light illumination and thereby to emit therapeutic light. Herein, the solar absorption layer is capable of converting incident light into electrical energy to drive the organic emission layer, and the organic emission layer may be disposed between the solar absorption layer and the pharmaceutical drug layer.

In the present invention, the fluorescent layer may include an oxidant, a fluorescent dye and an ester compound. Preferably, the fluorescent layer has an insulating element disposed therein to isolate the oxidant from the fluorescent dye and the ester compound. Herein, the fluorescent dye and the ester compound may be disposed inside the insulating element, while the oxidant may be disposed outside the insulating element. Alternatively, the oxidant may be disposed inside the insulating element, while the fluorescent dye and the ester compound may be disposed outside the insulating element. Accordingly, when using the phototherapy patch according to the present invention, users can break the insulating element to mix the oxidant, the fluorescent dye and the ester compound so as to cause a chemical reaction through which the fluorescent dye can emit therapeutic light. Herein, the ester compound may be an oxalate ester compound, and the oxidant may be hydrogen peroxide. In addition, the fluorescent layer may be capable of emitting therapeutic light within the wavelength range of about 400-470 nm, 500-550 nm, 550-600 nm, 600-700 nm, 700-1000 nm or the mixture thereof.

In the present invention, the organic emission layer may include: a first electrode layer disposed over the pharmaceutical drug layer; an organic material layer disposed on the first electrode layer; and a second electrode layer disposed on the organic material layer. Herein, the organic emission layer may be capable of emitting therapeutic light within the wavelength range of about 400-470 nm, 500-550 nm, 550-600 nm, 600-700 nm, 700-1000 nm or the mixture thereof. Additionally, the solar absorption layer may include: a photoelectric conversion layer disposed on the second electrode layer; and a third electrode layer disposed on the photoelectric conversion layer and electrically connected to the first electrode layer. Herein, the third electrode may be electrically connected to the first electrode layer via a circuit. Accordingly, when users attach the phototherapy patch according to the present invention to skin, photovolatic effect in the solar absorption layer can be driven via illumination of ambient light to convert incident light into electrical energy, such that the organic emission layer is driven to emit therapeutic light.

The phototherapy patch according to the present invention may further include: an isolating layer disposed between the pharmaceutical drug layer and the spontaneous emission layer to isolate the pharmaceutical drug layer from the spontaneous emission layer. Herein, the isolating layer may be made of a light-transmissive material to allow the therapeutic light emitted from the spontaneous emission layer to pass through the isolating layer and to illuminate the sites to be treated, such that the phototherapeutic effect can be achieved.

The phototherapy patch according to the present invention may further include: a passivation layer covering the pharmaceutical drug layer, the spontaneous emission layer and the isolating layer to protect the pharmaceutical drug layer, the spontaneous emission layer and the isolating layer from being damaged. Herein, the passivation layer may be made of a flexible plastic material to be suitable for flexible design.

The phototherapy patch according to the present invention may further include: a release film disposed on the second surface of the adhesive layer to protect the second surface of the adhesive layer. Herein, when using the phototherapy patch, users can remove the release film and attach the phototherapy patch to sites to be treated.

In the present invention, the pharmaceutical drug layer may include at least one active component with pharmaceutical or cosmetological effects. For example, the pharmaceutical drug layer may include retinoic acid, steroid, arbutin, azelaic acid, sulfur, salicylic acid, benzoyl peroxide or a mixture thereof. Preferably, the pharmaceutical drug layer is light transmissive, such that therapeutic light can pass through the pharmaceutical drug layer and illuminate sites to be treated.

In the present invention, the first electrode layer may be a light-transmissive conductive layer, such that therapeutic light can pass through the first electrode layer and illuminate sites to be treated. The material of the first electrode may be, for example, ITO, IZO, AZO or ZnO.

In the present invention, the second electrode layer may be a lightproof conductive layer to inhibit ambient light to get into the organic material layer from the solar absorption layer.

In the present invention, the third electrode layer may be a light-transmissive conductive layer, such that ambient light can pass through the third electrode layer and cause photovolatic effect in the solar absorption layer. The material of the third electrode layer include, for example, ITO, IZO, AZO, ZnO and so on.

In the present invention, the passivation layer is preferably made of a light-transmissive material in the case that the spontaneous emission layer is driven via light illumination and emits therapeutic light, such that ambient light can arrive at the interior of the phototherapy patch to drive the spontaneous emission layer to emit therapeutic light. If the spontaneous emission layer is driven via a chemical reaction and emits therapeutic light, the passivation layer may be made of a light-transmissive or lightproof material.

In the present invention, the adhesive layer may be made of a light-transmissive adhesive material, such that the phototherapy patch can be adhered to skin to be treated via the second surface of the adhesive layer and therapeutic light can pass through the adhesive layer to illuminate sites to be treated.

As mentioned-above, the present invention can combine pharmaceutical drugs and phototherapy and maintain the thin appearance of the patch to achieve multiple therapeutic effects and accelerate therapy. Thereby, the phototherapy patch according to the present invention can be applied to medical treatment and cosmetology, such as wound healing, spot removal, and acne treatment.

DETAILED DESCRIPTION OF THE PREFERRED EMBODIMENT

Hereafter, examples will be provided to illustrate the embodiments of the present invention. Other advantages and effects of the invention will become more apparent from the disclosure of the present invention. Other various aspects also may be practiced or applied in the invention, and various modifications and variations can be made without departing from the spirit of the invention based on various concepts and applications.

EXAMPLE 1

Figure 1:
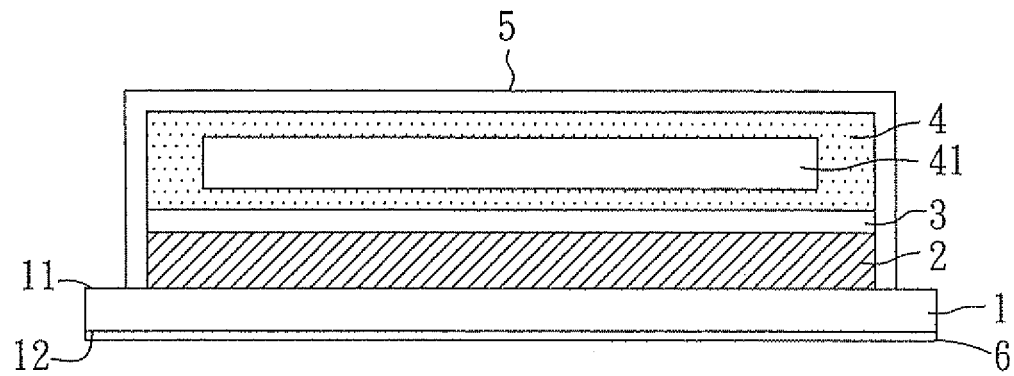
FIG. 1 shows a cross-sectional view of a phototherapy patch according to a preferred example of the present invention.

With reference to FIG. 1, there is shown a cross-sectional view of a phototherapy patch according to a preferred example of the present invention.

As shown in FIG. 1, the phototherapy patch according to the present example includes: an adhesive layer 1, a pharmaceutical drug layer 2, an isolating layer 3, a spontaneous emission layer 4, a passivation layer 5 and a release film 6. In detail, the adhesive layer 1 has a first surface 11 and an opposite second surface 12. Herein, the pharmaceutical drug layer 2 is disposed on the first surface 11 of the adhesive layer 1, while the release film 6 is disposed on the second surface 12 of the adhesive layer 1. Additionally, the isolating layer 3 and the spontaneous emission layer 4 are laminated on the pharmaceutical drug layer 2 in sequence, such that the isolating layer 3 is disposed between the pharmaceutical drug layer 2 and the spontaneous emission layer 4. Finally, the passivation layer 5 covers the pharmaceutical drug layer 2, the isolating layer 3 and the spontaneous emission layer 4 to protect the inner structure of the phototherapy patch from being damaged by external force.

The passivation layer 5 used in the present example is made of a flexible plastic material to cover the pharmaceutical drug layer 2, the isolating layer 3 and the spontaneous emission layer 4 and thereby to protect pharmaceutical drug layer 2, the isolating layer 3 and the spontaneous emission layer 4 from being damaged by external force.

The spontaneous emission layer 4 according to the present example is a fluorescent layer, which includes an oxidant, a fluorescent dye and an ester compound and has an isolating element 41 disposed therein to isolate the oxidant from the fluorescent dye and the ester compound. In the present example, the oxidant and the ester compound are hydrogen peroxide and phenyloxalate ester, respectively. Herein, hydrogen peroxide is disposed inside the isolating element 41, and phenyloxalate ester and the fluorescent dye are disposed outside the isolating element 41. Accordingly, when using the phototherapy patch according to the present example, users can break the insulating element 41 to mix the oxidant inside the insulating element 41 with the fluorescent dye and phenyloxalate ester outside the insulating element 41 so as to cause a chemical reaction through which the fluorescent dye can emit therapeutic light. Herein, the present example uses a fluorescent dye capable of emitting red light (its wavelength ranges from about 600 nm to 700 nm) to achieve the effects of wound healing and whitening. In addition, the pharmaceutical drug layer 2 according to the present example includes various kinds of active components with whitening effect and is light transmissive. Accordingly, the spontaneous emission layer 4 and the pharmaceutical drug layer 2 can simultaneously act on users and achieve dual whitening effects to accelerate whitening.

The isolating layer 3 used in the present example is used to isolate the spontaneous emission layer 4 from the pharmaceutical drug layer 2, and is made of a light-transmissive material to allow therapeutic light from the spontaneous emission layer 4 to pass through the isolating layer 3 and illuminate the site to be treated.

The adhesive layer 1 according to the present example is made of a light-transmissive adhesive material. Accordingly, the phototherapy patch of the present example can be adhered to skin via the second surface 12 of the adhesive layer 1, and the therapeutic light from the spontaneous emission layer 4 can pass through the adhesive layer 1 and illuminate the site to be treated. Herein, before application of the phototherapy patch, the release film 6 covers the second surface 12 of the adhesive layer 1, and users can remove the release film 6 to attach the phototherapy patch to sites to be treated.

EXAMPLE 2

Figure 2:
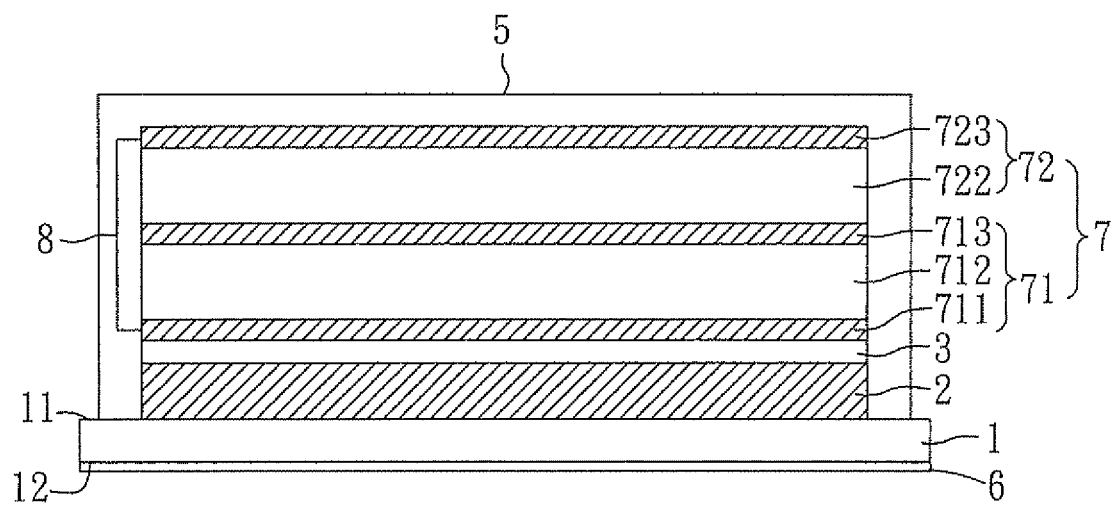
FIG. 2 shows a cross-sectional view of a phototherapy patch according to another preferred example of the present invention.

With reference to FIG. 2, there is shown a cross-sectional view of a phototherapy patch according to another preferred example of the present invention.

As shown in FIG. 2, the phototherapy patch according to the present example is the same as that illustrated in the example 1, except that the spontaneous emission layer 7 according to the present example is driven via light illumination and emits therapeutic light. In detail, as shown in FIG. 2, the spontaneous emission layer 7 according to the present example includes an organic emission layer 71 and a solar absorption layer 72. Herein, the organic emission layer 71 is disposed between the solar absorption layer 72 and the isolating layer 3, and the solar absorption layer 72 can convert incident light into electrical energy so as to drive the organic emission layer 71 to emit therapeutic light.

In the present example, the organic emission layer 71 includes: a first electrode layer 711 disposed on the isolating layer 3; an organic material layer 712 disposed on the first electrode layer 711; and a second electrode layer 713 disposed on the organic material layer 712. Herein, the present example uses a light-transmissive conductive layer as the first electrode layer 711 to allow therapeutic light to pass through the first electrode layer 711 and to illuminate sites to be treated. Additionally, the second electrode layer 713 is a lightproof conductive layer to inhibit ambient light to get to the organic material layer 712 from the solar absorption layer 72.

The solar absorption layer 72 used in the present example includes: a photoelectric conversion layer 722 disposed on the second electrode layer 713; and a third electrode layer 723 disposed on the photoelectric conversion layer 722 and electrically connected to the first electrode layer 711 via a circuit 8. Herein, the present example uses a light-transmissive layer as the third electrode layer 723, such that ambient light can pass through the third electrode layer 723 to cause photovolatic effect in the solar absorption layer 72. Besides, the passivation layer 5 of the present example is made of a light transmissive and flexible plastic material, such that ambient layer can arrive at the interior of the phototherapy patch to drive photovolatic effect in the solar absorption layer 72.

The pharmaceutical drug layer 2 according to the present example includes various kinds of active components for inhibiting activity of propionibacterium acne, and the organic emission layer 71 can emit blue light of about 400 nm-470 nm to accelerate acne treatment and to relieve the symptoms. Accordingly, when users attach the phototherapy patch according to the present example to skin, photovolatic effect in the solar absorption layer 72 can be driven via illumination of ambient light to convert incident light into electrical energy, such that the organic emission layer 71 is driven to emit therapeutic light, which is combined with the pharmaceutical drug layer 2 to achieve dual effects from phototherapy and pharmaceutical drugs.

The above examples are intended for illustrating the embodiments of the subject invention and the technical features thereof, but not for restricting the scope of protection of the subject invention. The scope of the subject invention is based on the claims as appended.

What is claimed is:

1. A phototherapy patch, comprising:
    an adhesive layer, having a first surface and an opposite second surface;
    a pharmaceutical drug layer, disposed on the first surface of the adhesive layer; and
    a spontaneous emission layer, disposed over the pharmaceutical drug layer and capable of emitting therapeutic light via light illumination; and
    wherein the spontaneous emission layer comprises a solar absorption layer and an organic emission layer, the solar absorption layer is capable of converting incident light into electrical energy to drive the organic emission layer to emit therapeutic light, and the organic emission layer is disposed between the solar absorption layer and the pharmaceutical drug layer.

2. The phototherapy patch as claimed in claim 1, further comprising:
    an isolating layer, disposed between the pharmaceutical drug layer and the spontaneous emission layer.

3. The phototherapy patch as claimed in claim 2, further comprising: a passivation layer, covering the pharmaceutical drug layer, the spontaneous emission layer and the isolating layer.

4. The phototherapy patch as claimed in claim 1, further comprising: a release film, disposed on the second surface of the adhesive layer.

5. The phototherapy patch as claimed in claim 1, wherein the organic emission layer comprises: a first electrode layer disposed over the pharmaceutical drug layer; an organic material layer disposed on the first electrode layer; and a second electrode layer disposed on the organic material layer.

6. The phototherapy patch as claimed in claim 5, wherein the solar absorption layer comprises: a photoelectric conversion layer disposed on the second electrode layer; and a third electrode layer disposed on the photoelectric conversion layer and electrically connected to the first electrode layer.

7. The phototherapy patch as claimed in claim 6, wherein the third electrode is electrically connected to the first electrode layer via a circuit.

8. The phototherapy patch as claimed in claim 6, wherein the third electrode layer is a light-transmissive conductive layer.

9. The phototherapy patch as claimed in claim 5, wherein the first electrode layer is a light-transmissive conductive layer.

10. The phototherapy patch as claimed in claim 5, wherein the second electrode layer is a lightproof conductive layer.

11. The phototherapy patch as claimed in claim 1, wherein the spontaneous emission layer is capable of emitting therapeutic light within the wavelength range of 400-470 nm, 500-550 nm, 550-600 nm, 600-700 nm or 700-1000 nm.

* * * * *